(12) United States Patent
Kuehner et al.

(10) Patent No.: US 9,138,251 B2
(45) Date of Patent: Sep. 22, 2015

(54) INSTRUMENT FOR WATER JET SURGERY

(71) Applicant: ERBE ELEKTROMEDIZIN GMBH, Tuebingen (DE)

(72) Inventors: Ralf Kuehner, Stuttgart (DE); Stefanie Schmidt, Pliezhausen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 191 days.

(21) Appl. No.: 13/682,833

(22) Filed: Nov. 21, 2012

(65) Prior Publication Data
US 2013/0158544 A1    Jun. 20, 2013

(30) Foreign Application Priority Data

Dec. 14, 2011   (EP) .................................. 11193542

(51) Int. Cl.
| | |
|---|---|
| *A61B 17/32* | (2006.01) |
| *A61B 17/3203* | (2006.01) |
| *A61B 18/14* | (2006.01) |
| *A61B 18/12* | (2006.01) |
| *A61B 17/00* | (2006.01) |
| *A61B 19/00* | (2006.01) |

(52) U.S. Cl.
CPC ............ *A61B 17/3203* (2013.01); *A61B 18/12* (2013.01); *A61B 18/1477* (2013.01); *A61B 2017/00539* (2013.01); *A61B 2018/1475* (2013.01); *A61B 2019/481* (2013.01)

(58) Field of Classification Search
USPC ........ 606/156, 166–168, 170; 604/41, 19, 22, 604/70
See application file for complete search history.

(56) References Cited

U.S. PATENT DOCUMENTS

| | | | |
|---|---|---|---|
| 3,699,957 A * | 10/1972 | Robinson ...................... | 128/843 |
| 5,505,729 A | 4/1996 | Rau | |
| 6,168,594 B1 * | 1/2001 | LaFontaine et al. ............ | 606/41 |
| 2002/0111644 A1 * | 8/2002 | Shuman et al. ................ | 606/167 |
| 2006/0184190 A1 * | 8/2006 | Feiler et al. .................... | 606/185 |
| 2011/0028887 A1 * | 2/2011 | Fischer et al. .................. | 604/22 |
| 2011/0270240 A1 * | 11/2011 | Shiu et al. ....................... | 606/33 |

FOREIGN PATENT DOCUMENTS

| | | |
|---|---|---|
| CA | 2497897 A1 | 4/2004 |
| CN | 101983038 A | 3/2011 |
| DE | 10 2009 017636 A1 | 10/2010 |
| EP | 0 530 400 B1 | 12/1996 |
| EP | 0 536 440 B1 | 5/1997 |
| JP | H05-253238 A | 10/1993 |
| JP | H09-224951 A | 9/1997 |
| JP | 2007-507261 A | 3/2007 |
| JP | 2011-516131 A | 5/2011 |

(Continued)

*Primary Examiner* — Paula J Stice
(74) *Attorney, Agent, or Firm* — Dickstein Shapiro LLP

(57) ABSTRACT

A surgical instrument for performing water jet surgical operations comprises a nozzle that can be moved via a hydraulic actuator out of a retracted or passive position into a moved-forward or active position. The actuation is accomplished using hydraulic fluid that is supplied to the instrument head via a tube and/or hose. The fluid (e.g., a sodium chloride solution) that is to be injected into the tissue can be used as the hydraulic fluid that is supplied to the nozzle. High-frequency (HF) current can additionally be applied to the nozzle. The HF current can be conducted to the nozzle via a line extending through the fluid conducting element or via the electrolyte present therein.

15 Claims, 4 Drawing Sheets

(56) References Cited

FOREIGN PATENT DOCUMENTS

| RU | 2 069 986 C1 | 12/1996 |
| RU | 2 124 323 C1 | 1/1999 |
| RU | 2 134 554 C1 | 8/1999 |
| SU | 1690717 A1 | 11/1991 |
| WO | WO 2009/009274 A2 | 1/2009 |
| WO | WO 2009/121563 A2 | 10/2009 |
| WO | WO 2010/118818 A1 | 10/2010 |

* cited by examiner

//...
INSTRUMENT FOR WATER JET SURGERY

RELATED APPLICATION

This application claims priority to European patent application EP 11 193 542.5, filed on Dec. 14, 2011, which is hereby incorporated by reference in its entirety.

TECHNICAL FIELD

Embodiments of the invention relate to a surgical instrument for water jet surgery, optionally in combination with high-frequency (HF) surgery.

BACKGROUND

European publication EP 0 530 400 B1 discloses an instrument for high-frequency (HF) surgery and for cutting and coagulating with HF current; the instrument comprises a flexible shaft having a retractable, needle-shaped HF electrode arranged on its tip. A cable extending through the shaft is used for mechanical movement and for supplying power to said electrode. That is, the cable is used for the electrical supply of the electrode, as well as for the transmission of a mechanical movement to the electrode.

From European publication EP 0 536 440 B1 it has additionally been known to design the shaft as a fluid conducting element through which rinsing fluids can be supplied to the HF electrode and which can also be used for suctioning.

Furthermore, Canadian publication CA 2497897 A1 discloses an endoscopic instrument that has scissors attached at its distal end. The latter is actuated using fluid cylinders that are connected via a fluid conducting mechanism to a hydraulic actuation member on the proximal end.

In addition, it has been known from German publication DE 10 2009 017 636 A1 to use a fluid jet arrangement comprising, on its one distal end, a nozzle for performing dissection and/or needleless injection of tissue. In addition, it has been known from this publication to provide such a fluid jet arrangement with an HF electrode for performing additional treatment measures such as, for example, the cutting and/or coagulating of tissue using HF current. In doing so, the surgeon can selectively inject fluid jets or HF current into the tissue to initiate the desired effect, without the need to change the instrument to accomplish this. This shortens the operating time and simplifies the handling of the instrument.

SUMMARY

It is an object of the embodiments disclosed herein to further improve a fluid surgical instrument with respect to its handlability.

The instrument in accordance with the present disclosure comprises an instrument head that supports a movable nozzle. This nozzle can be moved back and forth between a first position and a second position. Desirably, this movement is linear. However, different movements, e.g., pivoting or rotating movements are also possible. The two positions may be an active position and a passive position. The movability of the nozzle between the active position and the passive position makes it possible for the nozzle to be brought into a protected position such as, for example, when it is being positioned into a body cavity of the patient or in the tissue of the patient. Consequently, the nozzle may be configured as an extremely fine (e.g., slim) needle. There is no danger that the needle will bend or break in the tissue when the instrument is being positioned and when the nozzle is in its protected position, e.g., in a retracted position (passive position).

To perform a treatment, the nozzle may be brought into the active position. For example, a needle-shaped nozzle can be moved forward in the longitudinal direction and thus be free and exposed to the tissue. In this case, the nozzle may act as an HF electrode, for example, to inject HF current into the tissue and bring about a desired surgical effect. It is also possible to use the nozzle for ejecting a water jet. Desirably, this is also accomplished in the moved-forward position of the nozzle (i.e., in the active position). Alternatively, water jet injection is also possible with the nozzle in the retracted position. This alternative lies within the scope of various options for the disclosed embodiments.

In accordance with the present disclosure, the nozzle is in connection with a hydraulic actuator, by which the nozzle can be moved back and forth between at least two positions, i.e., between an active position and a passive position. The hydraulic actuator comprises a fluid chamber that is loaded with hydraulic fluid. The fluid chamber provided in or on the instrument head communicates via a fluid conducting element, e.g., a tube, hose or a combination of the two, with an instrument connector body. From the latter, the hydraulic fluid is conveyed through the fluid conducting element to the actuator that, as a result, moves the nozzle into the active position or into the passive position.

Desirably, the actuator is used to move the nozzle into the active position while it may be biased in its retracted position or passive position by a spring mechanism. This particularly applies when the nozzle is supported so as to be linearly movable. Desirably, the nozzle is supported so as to be linearly movable along a jet direction defined by said nozzle. If the nozzle has the shape of a needle, it is moved along its longitudinal direction.

Desirably, the hydraulic actuator may be designed as a plunger/cylinder unit. However, other actuators are possible such as, e.g., balloon arrangements or the like that convert the change of fluid pressure or fluid volume to a mechanical motion. The obtained drive motion may be a pushing, pivoting or pulling motion.

Desirably, a fluid generally recognized as physiologically safe is provided as the hydraulic medium; for example, a sodium chloride solution, desirably a physiological cooking salt solution, may be used. This may be the fluid to be ejected by the nozzle or a fluid conveyed in separate channels. The fluid pressure is varied using a regulating device for the hydraulic actuation of the actuator. This regulating device may be actuated, e.g., manually, or it may also consist of other technical mechanisms such as pumps or the like. The nozzle may be connected to a source of high-frequency current. The HF current (or a HF voltage) can be conducted via a suitable electrical conducting mechanism from the instrument connector body to the instrument head and, from there, to the nozzle that acts as the electrode. Optionally, it is also possible to provide separate electrodes. For electrical conduction, metal cord (insulated or not) may extend through the fluid conducting element. However, it is also possible to utilize the hydraulic fluid present in the fluid conducting element as an electrical conductor, particularly when the fluid is an electrolyte (e.g., NaCl solution). In doing so, it is possible to construct highly flexible and very slim instruments for water jet surgery and, in particular, for combined water jet/electrical surgery.

Desirably, the nozzle has a nozzle channel that communicates with the fluid chamber and thus with the (first) fluid conducting element. It is also possible to provide a second fluid conducting element that supplies fluid to the nozzle, whereby the other (first) fluid conducting element is used only for the actuation of the actuator. The two fluid conducting elements may be arranged coaxially relative to each other (i.e., one in the other) or in another arrangement such as, for example, they may be arranged parallel to each other.

Desirably, the nozzle is associated with a valve that is capable of clearing or blocking the connection from the fluid conducting feed element to the nozzle. The valve may be actuated electrically or hydraulically. For example, the valve may be actuated via the supplied HF voltage. It may also be actuated by way of a direct voltage that is superimposed on the HF voltage. Alternatively, a control voltage may be applied to the valve via a separate line. In addition, the valve may be actuated by the fluid pressure that is applied to the nozzle and/or to the hydraulic actuator.

BRIEF DESCRIPTION OF THE DRAWINGS

Hereinafter, exemplary embodiments of the invention are explained in greater detail with reference to drawings, in which.

DETAILED DESCRIPTION

Figure 1:
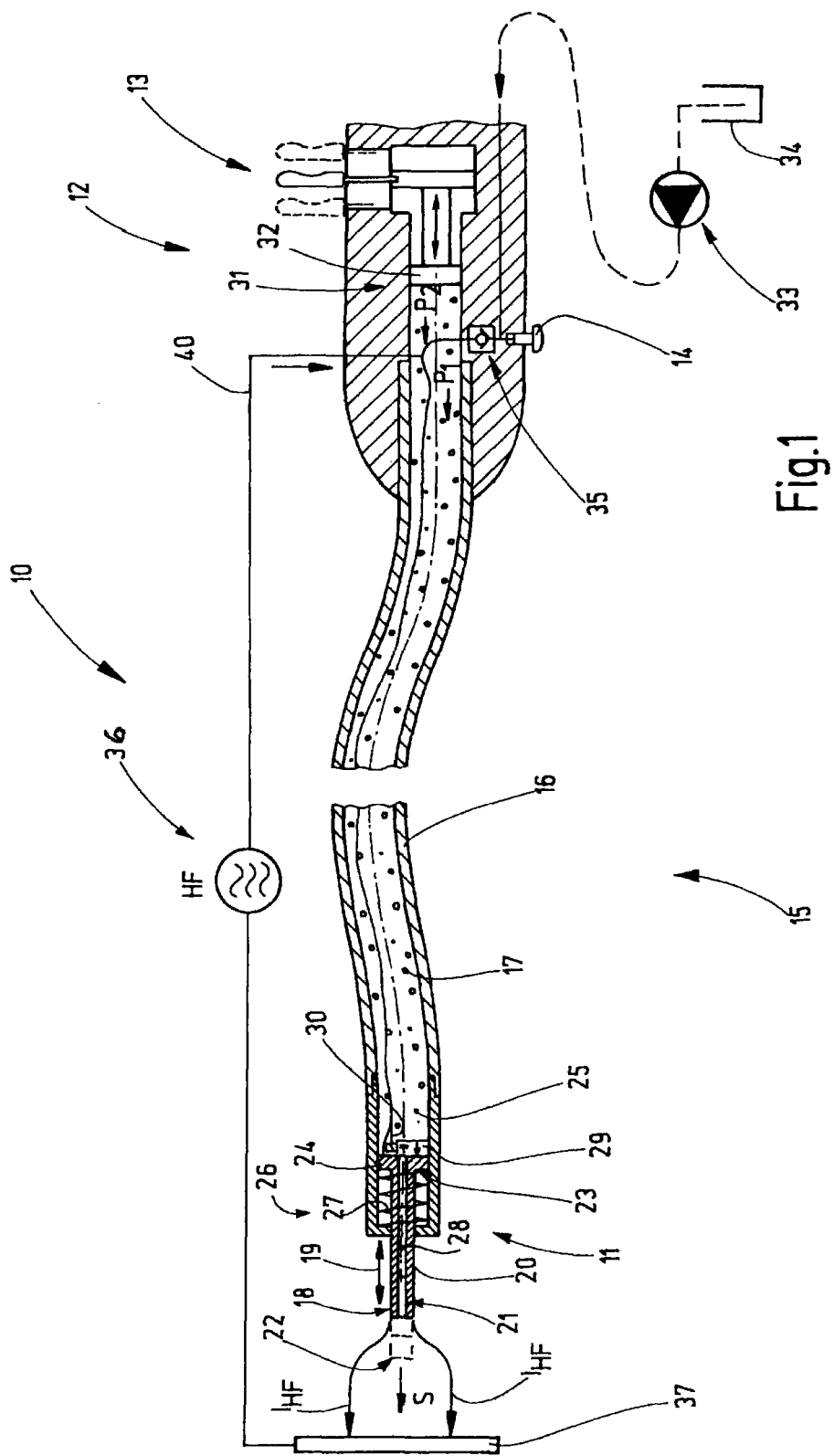
FIG. 1 illustrates a longitudinal section of a first embodiment of a combined water jet/HF surgery instrument disclosed herein.

FIG. 1 is a schematic representation of an instrument 10 that is at least suitable for performing water jet surgery operations. The instrument 10 comprises an instrument head 11 that is the distal end of the instrument 10 viewed from the perspective of the surgeon. The proximal end of the instrument 10 is an instrument connector body 12 that can house actuating elements 13, 14 for the actuation or deactuation of the instrument 10. The instrument connector body 12 may be designed as a holding grip or in another manner.

A fluid conducting element 15 is arranged between the instrument connector body 12 and the instrument head 11. For example, the fluid conducting element 15 comprises a flexible hose 16, a rigid or bendable tube, or a combination of hose and tube sections, or other mechanism, for enclosing a channel 17 that may contain fluid. The fluid is a hydraulic fluid. In the present embodiment, the fluid is desirably a sodium chloride solution, e.g., a physiological cooking salt solution. A nozzle 18 is provided on the instrument head 11, the nozzle 18 is supported so as to be movable in the longitudinal direction (indicated by arrow 19).

Desirably, the nozzle 18 is associated with an elongated, needle-like tube 20, in which case a nozzle body 21 may be arranged on the end of the tube 20. Desirably, the nozzle 18 is used to eject a thin fluid jet capable of separating tissue layers from each other or perforating them and is thus capable of injecting fluid into the tissue. The fluid jet may be a laminar or turbulent, e.g., conical or differently formed, fluid jet. Desirably, the tube 20 consists of metal.

The nozzle 18 can be moved between a retracted, inactive/passive position and a moved-forward, active position along a jet direction S. FIG. 1 shows the retracted position in which the nozzle 18 is at least partially retracted into the instrument head 11. The nozzle 18 can be axially moved out of the instrument head 11. In FIG. 1, a moved-forward, active position is indicated by dashed lines 22.

A hydraulic actuator 23 is provided to move the nozzle 18 into the instrument head 11. The actuator 23 consists, for example, of a metal plunger 24 bordering at least one side of a fluid chamber 25. Desirably, the fluid chamber 25 consists of an electrically insulating material, desirably a synthetic material, or is otherwise insulated relative to the outside of the chamber.

In this exemplary embodiment, the fluid chamber 25 is a cylindrical chamber, e.g., having a circular cross-section. The movable plunger 24, which is seated and sealed in the fluid chamber 25, is desirably rigidly connected to the nozzle 18 and the tube 20; the tube 20 can be viewed as a plunger rod. Optionally, the plunger 24 is associated with a spring mechanism 26, e.g., in the form of a helical spring 27, that biases the plunger 24, and the nozzle 18, into a retracted/passive position. A nozzle channel 28 extends through the nozzle 18 and the tube 20, as well as through the plunger 24, whereby the fluid to be ejected by the nozzle 18 reaches the nozzle orifice through said channel 28.

Optionally, yet desirably, the nozzle 18 is associated with a controlled valve 29. The valve 29 comprises at least two valve settings, i.e., closed and open. The valve 29 is interposed between the nozzle channel 28 and channel 17. In the present example embodiment, the valve 29 is controlled via an electrical line 30. This line 30 extends through channel 17 from the instrument head 11 to the instrument connector body 12. Line 30 may be a flexible, insulated cord. However, line 30 may also be a non-insulated, flexible electrical conductor that is in electrical contact with the electrolyte present in the channel 17.

The instrument connector body 12 comprises a regulating device 21 that may be a pump device which, when actuated, is used to displace a prespecified amount of fluid and transport the fluid through the channel 17 to the instrument head 11. For example, this regulating device 31 is shown as a plunger 32 that is slidably supported in a bore, where the plunger 32 can be used for applying a pressure $P_2$ to the fluid column standing in the channel 17. The actuating element 13 may be used, for example, for sliding the plunger 32 back and forth; the actuating element 13 being manually actuatable by the surgeon. However, it is also possible to provide other actuating devices such as pull-type magnets or the like.

The instrument 10 is connected to an apparatus that is not specifically shown in FIG. 1. The apparatus comprises a pump device 33 that is used to convey the fluid (e.g., NaCl solution) to be fed to the nozzle 18 from a supply 34 to the instrument connector body 12 and from there to the instrument head 11 and nozzle 18 via the fluid conducting element 15. For controlling the fluid feed flow to or into channel 17, a valve 35 that can be opened using an actuating element 14, e.g., manually, may be provided. The pump device 33 desirably uses a conveying pressure $P_1$ that is used to generate the fluid jet exiting from the nozzle 18.

Line 30 can be used for connecting valve 35 to valve 29 to control valve 29. In this manner, valve 29 can be opened whenever the respective fluid is moved under pressure into the channel 17 by way of the actuating element 14.

Optionally, the instrument 10 may additionally act as an HF surgical instrument and may be connected to an HF power source or an HF voltage source. The HF voltage source 36 may be part of an apparatus supplying the instrument 10 with HF power (not specifically illustrated). The HF voltage source 36 is connected to a neutral electrode 37, said neutral electrode being desirably connected to the patient over a large surface, and to the instrument connector body 12, whereby the HF voltage is conducted to the instrument head 11 via said instrument connector body 12. Again, this can be accomplished using line 30 that extends through the fluid conducting element 15. Alternatively, line 30 may also be embedded in the wall of the fluid conducting element 15.

In surgical use, at least the instrument head 11 and part of the fluid conducting element 15 of the instrument head 10 are inserted into a body cavity or into the tissue of a patient. This may be done endoscopically, laparoscopically or in the open surgical field. When the instrument 10 is being inserted, the nozzle 18 is in a retracted position in which the thin, needle-like tube 20 is positioned at least partially protected in the interior of the instrument head 11.

When the nozzle 18 is to be actuated, it is moved into a moved-forward position. To do so, the surgeon actuates the actuating element 13, which moves the plunger 32 forward to displace fluid. In other words, the regulating device 31 (or another appropriate pump device) is activated and pushes the plunger 24—via the coupling of the fluid column in the channel 17—against the force of the spring mechanism 26 in the distal direction. The nozzle 18 that has been moved forward can now be activated electrically and/or by a fluid-technical actuation (discussed below).

For electrical actuation, the HF generator 36 is actuated, e.g., by a foot switch, hand switch or the like, so that the nozzle 18 injects an HF current—on its external jacket or on parts thereof and/or on its front surface—into the tissue. In FIG. 1, this current is indicated by diverging arrows $I_{HF}$.

The fluid actuating element 14 is actuated for fluid-technical actuation. To accomplish this, additional electrolytes, e.g., NaCl solution, are conveyed into channel 17. At the same time, valve 29 is opened via line 30 so that a fluid jet can exit from the nozzle 18 and cause the desired effect. At the same time, the surgeon must hold the actuating element 13 in the moved-forward position or lock said element in the moved-forward position.

Valve 29 may be selectively actuated depending on various events and may be controlled via different mechanisms. Depending on the embodiment, line 30 may be a multi-wire line. If so, a first wire is used to actuate valve 29, e.g., as a function of the actuation of the element 14, or for opening the check valve 35 which, to this extent acts as a switch. Alternatively, valve 29 can be controlled via a separate actuating element.

Figure 2:
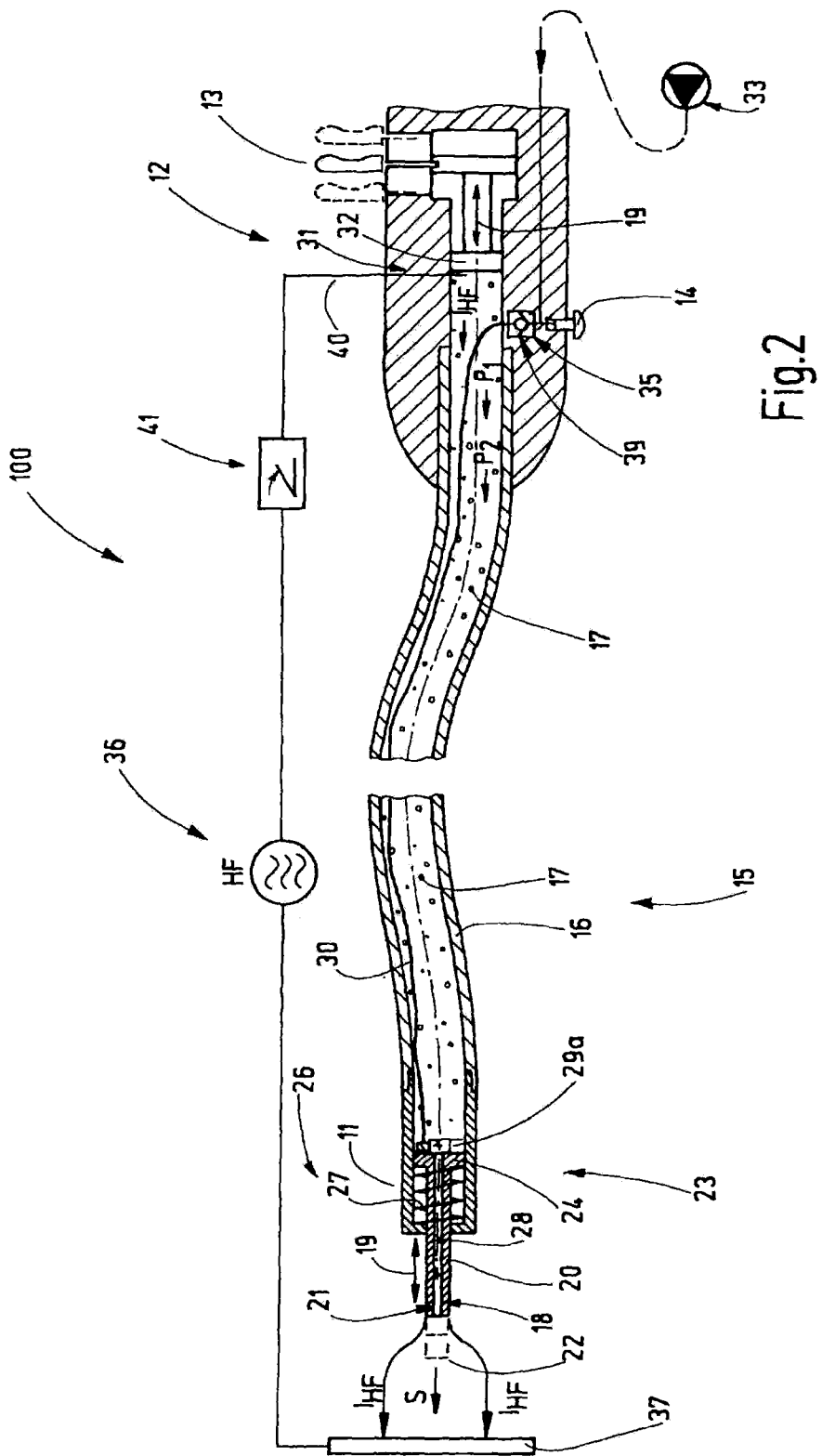
FIGS. 2 to 4 illustrate longitudinal sections of additional embodiments of combined water jet/HF surgery instruments disclosed herein.

FIG. 2 shows a modified embodiment of an instrument 100 in accordance with the present disclosure. To the extent that structurally or functionally identical or similar elements are provided in FIG. 2 (using the same reference signs as FIG. 1), reference is made to the above description. Different from the above-described embodiment, line 30 in the FIG. 2 embodiment is used only for the control of valve 29. Line 30 may thus be a single-wire line. For example, line 30 is controlled by a fluid pressure switch 39 that is used to detect whether or not the fluid pressure existing in the channel 17 exceeds a set pressure limit. FIG. 2 shows the fluid pressure switch 39 symbolically combined with the check valve 35. Alternatively, a separate switch may be provided, said switch responding to the actuation of the actuating element 14.

In the exemplary embodiment shown in FIG. 2, the electrically conductive fluid present in channel 17 is used to supply HF current to the nozzle 18. Desirably, the hydraulic fluid is a cooking salt solution that exhibits sufficient electrical conductivity. On the instrument connector body 12, the cooking salt solution is in electrical connection with an HF current supplying line 40 and, on the instrument head 11, said cooking salt solution is in connection with the plunger 24 and thus the nozzle 18. In addition, FIG. 2 shows a switch 41 for controlling the HF voltage source 36. The switch 41 is symbolically shown as a switch in line 40. Alternatively, the switch 41 can also directly control the HF source 36.

Figure 3:
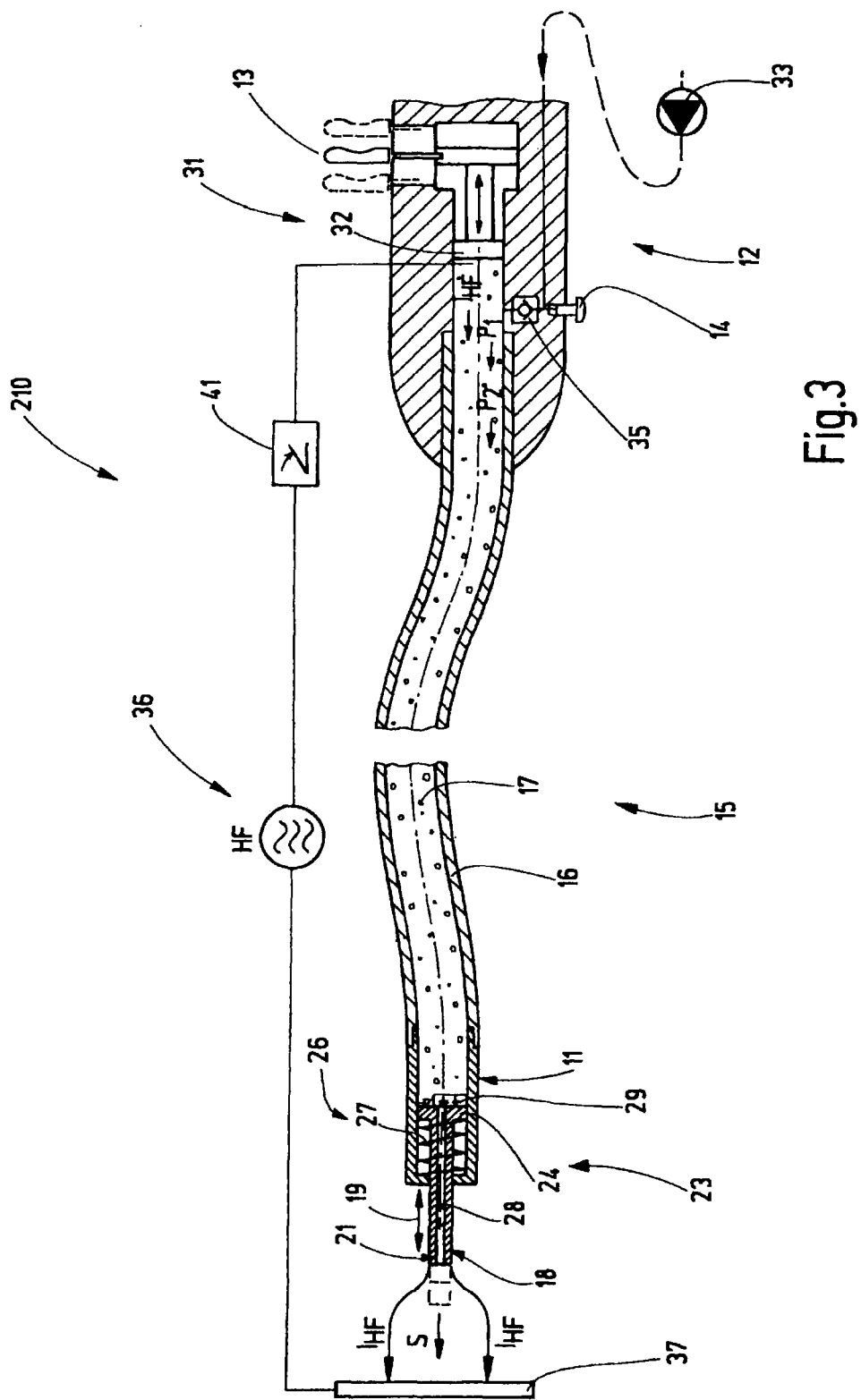

FIG. 3 shows another modified embodiment of an instrument 210 disclosed herein. To the extent that elements of FIG. 3 have the same structural and/or functional features as the elements of the previously described embodiments (using the same reference signs of FIGS. 1 and 2), reference is made to the above description. As shown, instrument 210 includes the actuation of valve 29 by the hydraulic pressure existing in channel 17. The HF supply to the plunger 24 and thus to the nozzle 18 can be accomplished, as shown, by the electrolyte (as in FIG. 2) or via a not illustrated line (as in FIG. 1). Valve 29 is configured such that it opens the connection between channel 17 and the nozzle channel 28 when the hydraulic pressure in channel 17 exceeds a threshold value. If the surgeon actuates the instrument 210 by actuating the actuating element 14, the pump device 33 conveys fluid at high pressure into channel 17 and opens valve 29 as soon as sufficient pressure has built up; as a result, a sharp jet exits the nozzle 18 in the direction shown by arrow S. In doing so, the nozzle 18 remains in the moved-forward, actuated position. After closing valve 35, e.g., when the operator releases the actuating element 14, valve 29 closes; the nozzle 18, however, remains moved-forward as long as the plunger 32 is held in the moved-forward position. If the surgeon or operator releases the actuating element 13, the spring 27 pushes the plunger 24 back into the retracted position. Thus, the plunger 32 returns to its retracted position as shown in FIG. 3.

Figure 4:
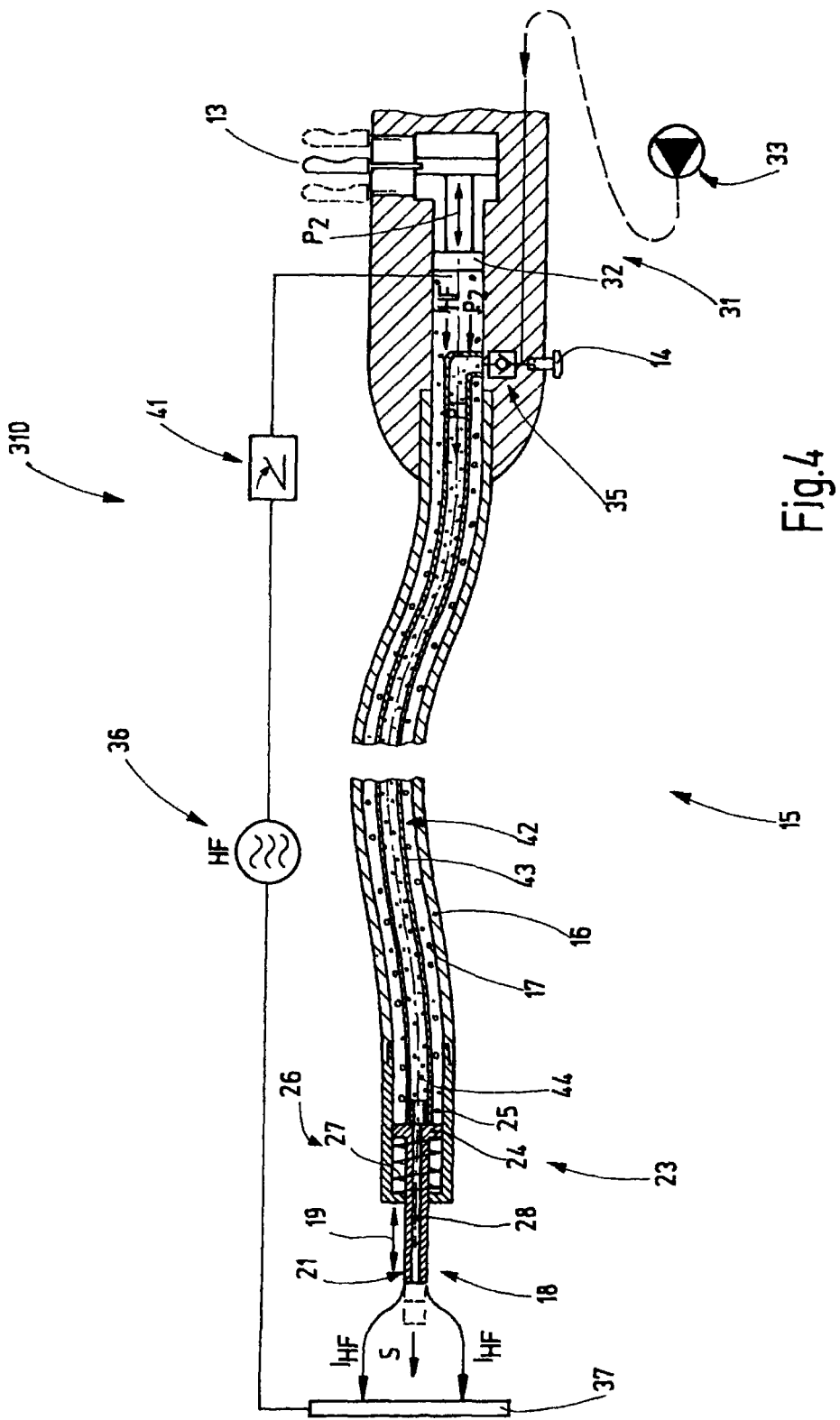

FIG. 4 illustrates another possible modification of an instrument 310 in accordance with the present disclosure. The instrument 310 does not need valve 29. In addition to the first fluid conducting element 15, the instrument 310 comprises a second fluid conducting element 42 that is configured, e.g., as a hose 43. The second fluid conducting element 42 may extend through channel 17 of the first fluid conducting element 15. The fluid conducting element 42 may be connected to the plunger 24 or an extension of the fluid conducting element. The interior channel 44 of the fluid conducting element 42 thus communicates with the nozzle channel 28. The proximal end of the fluid conducting element 42 may be connected to the pump device 33 by way of a valve controlled by the actuating element 14 and, e.g., by way of the check valve 35. In this embodiment, the check valve 35 is optional. Channel 17 is used only for actuating the plunger 24 or another actuator 23 and channel 44 is provided for supplying the nozzle 18. The (optional) feeding of HF current to the nozzle 18 may take place, as shown in FIG. 4, via the conductive electrolyte in channel 17 and/or via a separate electrical conductor (as shown in FIG. 1). The latter, in turn, may again be arranged in the wall of the hose 16 or may extend through the interior channel 17. It is also possible to combine the line (not shown) with the interior hose 43. Aside from these changes, the previous description of like/similar functions/elements applies to the FIG. 4 embodiment.

The present disclosure provides a surgical instrument 10, 110, 210, 310 for performing water jet surgical operations and comprises a nozzle 18 that can be moved, using a hydraulic actuator 23, out of a retracted or passive position into a moved-forward or active position. Actuation is accomplished using a hydraulic fluid that is supplied to the instrument head 11 via a tube 20 and/or a hose 43. The fluid (e.g., a sodium chloride solution) that is to be injected into the tissue can be used as the hydraulic fluid that is supplied to the nozzle 18. Desirably, HF current can additionally be applied to the nozzle 18. The HF current can be conducted to the nozzle via a line extending through the fluid conducting element 15 or via the electrolyte present therein.

What is claimed is:

1. A surgical instrument for water jet surgery, said instrument comprising:
   an instrument head containing a movably supported nozzle;
   an actuator arranged in the instrument head and being connected to the nozzle, said actuator comprising a fluid chamber;
   a first fluid conducting element in fluid communication with the fluid chamber, wherein the instrument head is in connection with an instrument connector body via the first fluid conducting element; and
   a valve arranged between the actuator and the first fluid conducting element and configured to selectively transfer a fluid to the nozzle for injection by the nozzle.

2. The instrument of claim 1, wherein the nozzle is linearly supported such that it is movable along a jet direction defined by said nozzle.

3. The instrument of claim 1, wherein the actuator is biased toward a retracted position by spring means.

4. The instrument of claim 1, wherein the nozzle is biased toward a retracted position by spring means.

5. The instrument of claim 1, further comprising a regulating device for hydraulic actuation of the actuator, said regulating device being provided in or on the instrument connector body.

6. The instrument of claim 5, wherein the regulating device is a pump.

7. The instrument of claim 1, wherein the nozzle is connected to a source of high-frequency current.

8. The instrument of claim 1, further comprising an electrical line extending from the instrument connector body to the nozzle.

9. The instrument of claim 8, wherein the electrical line is an electrolyte present in the first fluid conducting element.

10. The instrument of claim 1, wherein the nozzle comprises a nozzle channel and the fluid chamber is in fluid communication with the nozzle channel.

11. The instrument of claim 1, wherein the nozzle comprises a nozzle channel and the fluid chamber is in fluid communication with a second fluid conducting element.

12. The instrument of claim 11, wherein the second fluid conducting element communicates with a pump device that pumps fluid under pressure.

13. The instrument of claim 1, wherein the first fluid conducting element communicates with a pump device that pumps fluid under pressure.

14. The instrument of claim 1, wherein the valve can be electrically controlled.

15. The instrument of claim 1, wherein the valve can be hydraulically controlled.

* * * * *